(12) United States Patent
Kohani

(10) Patent No.: US 7,377,779 B2
(45) Date of Patent: May 27, 2008

(54) METHOD AND APPARATUS FOR REPOSITIONING TEETH

(75) Inventor: Kambiz Kohani, Carlsbad, CA (US)

(73) Assignee: Joe Dentist, Inc., San Diego, CA (US)

( * ) Notice: Subject to any disclaimer, the term of this patent is extended or adjusted under 35 U.S.C. 154(b) by 213 days.

(21) Appl. No.: 11/230,323

(22) Filed: Sep. 19, 2005

(65) Prior Publication Data

US 2007/0065771 A1   Mar. 22, 2007

(51) Int. Cl.
*A61C 19/00*   (2006.01)
(52) U.S. Cl. .......................................... 433/74; 433/52
(58) Field of Classification Search ................. 433/74, 433/52, 53, 213, 214; 434/263, 264
See application file for complete search history.

(56) References Cited

U.S. PATENT DOCUMENTS 4,083,114 A * 4/1978 Acevedo ........................ 433/2
4,952,151 A * 8/1990 Metcalfe ...................... 433/223
6,227,851 B1 * 5/2001 Chishti et al. ................ 433/24
6,499,997 B2   12/2002 Chishti et al.

* cited by examiner

*Primary Examiner*—John J Wilson
(74) *Attorney, Agent, or Firm*—Nydegger & Associates

(57) ABSTRACT

A system for straightening teeth includes a casting of teeth that is made of a rigid material, and a gum casting made of a flexible material that is joined to the teeth casting. A respective articulating tool for each tooth is provided with a post that is embedded into the tooth. Tooth moving components, accessible through the gum casting, are mounted on each post to selectively provide for left-right, fore-aft, and rotational tooth movements. In its operation, the system involves selectively orienting individual teeth in the teeth casting, to prepare a series of sequentially useable appliances that will straighten teeth in accordance with a preplanned procedure.

13 Claims, 2 Drawing Sheets

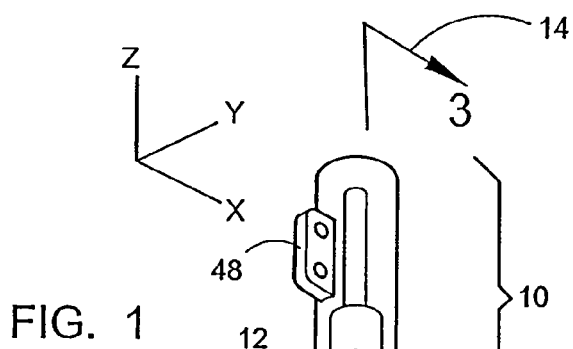
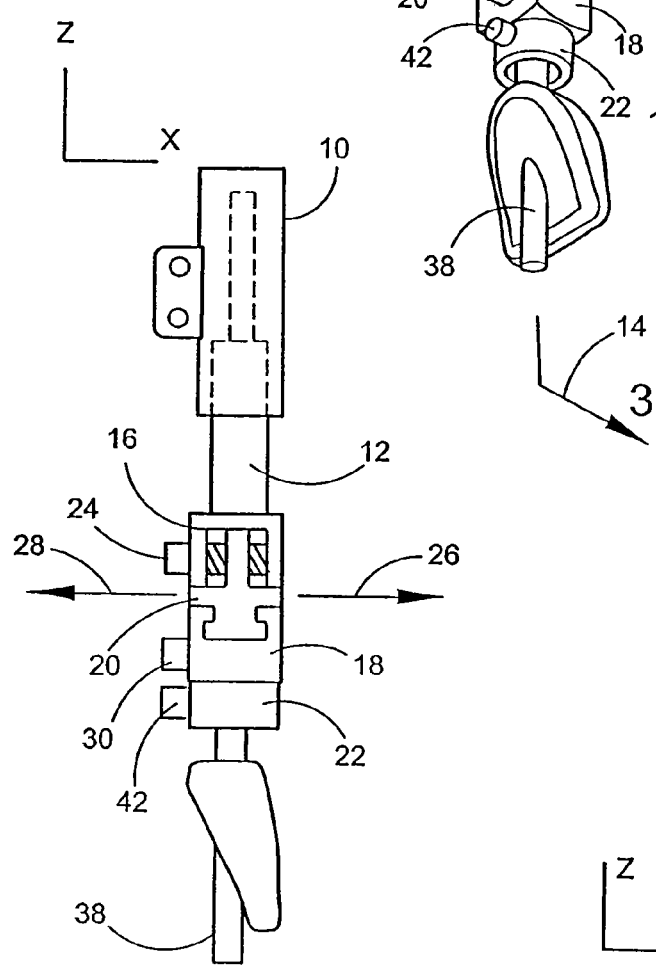
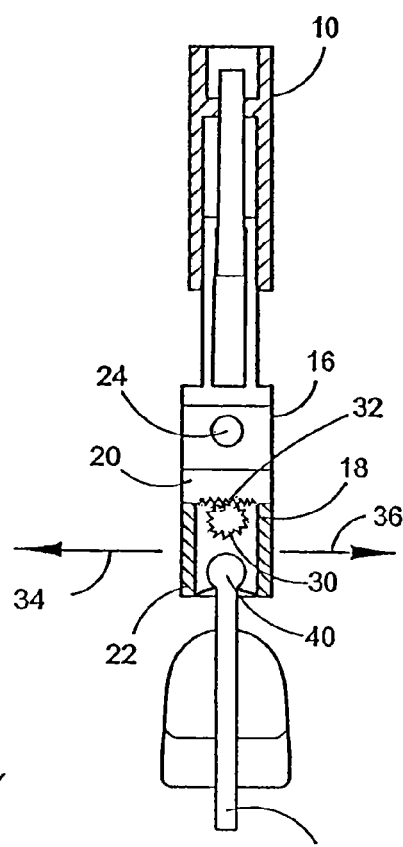

METHOD AND APPARATUS FOR REPOSITIONING TEETH

FIELD OF THE INVENTION

The present invention pertains generally to systems and devices for straightening teeth. More particularly, the present invention pertains to systems that involve preparing a series of sequentially useable appliances that will straighten teeth in accordance with a pre-planned procedure. The present invention is particularly, but not exclusively, useful as a plurality of articulating tools that can be selectively manipulated to respectively move individual teeth in a prosthetic dental structure for subsequent manufacture of an appliance that helps straighten teeth.

BACKGROUND OF THE INVENTION

It is a fact that not all persons are born with beautifully straight teeth. Nevertheless, for both health and beauty reasons, it is desirable that a person have a dental structure that is characterized by properly aligned (i.e. straight) teeth. Consequently, much effort is endured by many people to achieve this goal.

Heretofore, the use of braces has been widely accepted as a means for straightening teeth. Though effective for this purpose, braces necessitate many repeat visits to the dentist's office. Specifically, this happens because the dentist needs to gradually tighten the braces, rather than enforce a complete change in one sitting. That could be really painful. More recently, however, computer-generated systems have been developed that are intended to be used without requiring repeat visits to the dentist's office. Typically, these systems will include a series of appliances that are to be used sequentially, in a progression, to thereby incrementally and gradually align the teeth as desired. For example, U.S. Pat. No. 5,975,893, which issued to Chishti et al. for an invention entitled "Method and System for Incrementally Moving Teeth" discloses such a computer-generated system. Because they are computer-generated, however, such systems do not have the flexibility to selectively align individual teeth in a dental structure. More particularly, this cannot be done in a way that will remedy the specific dental alignment needs of a particular patient.

In light of the above, it is an object of the present invention to provide a mechanical device for reconfiguring a model dental structure, where each individual tooth in the dental structure can be selectively realigned, individually or collectively with other teeth in the structure. Another object of the present invention is to provide a system for reconfiguring a model dental structure that creates a series of teeth straightening appliances that are customized to incrementally remedy the specific dental alignment needs of a particular patient. Still another object of the present invention is to provide a mechanical device for reconfiguring a model dental structure that is easy to use, relatively simple to manufacture and commercially cost effective.

SUMMARY OF THE INVENTION

In accordance with the present invention, a device for reconfiguring a model dental structure includes a casting that comprises a plurality of teeth. Specifically, the teeth casting is made of a rigid material to provide an accurate physical replication of a patient's dental structure. Preferably, the rigid material is a hard durable urethane. Further, the device also includes a casting of the gum that is positioned in contact with the teeth casting. In contrast to the teeth casting, however, the gum casting is made of a relatively flexible material, such as a polyurethane elastomer. In addition to the teeth casting, and the gum casting, the device of the present invention also includes a support casting that is made of the same rigid material that is used for the teeth casting. In combination, the support casting is positioned in contact with the gum casting, with the gum casting positioned between the teeth casting and the support casting.

A plurality of elongated posts are individually embedded in the gum casting, and into a respective tooth in the teeth casting. More specifically, each elongated post has a first end and a second end, with the first end of the post being embedded in a respective tooth of the teeth casting. The second end of the post is distanced from the tooth, and extends into the gum casting.

A plurality of articulating tools is also provided for the device of the present invention. In particular, each articulating tool is respectively engaged with the second end of a post. Each articulating tool is also held in contact with the support casting to thereby stabilize the plurality of posts on the device. As intended for the present invention, each articulating tool can be accessed through the gum casting and manipulated to selectively, and individually, orient its respective tooth. Thus, the patient's original dental structure can be sequentially reconfigured to create a series of appliances that will successively realign and straighten the dental structure of a patient.

In greater structural detail, each articulating tool includes a main shaft that defines an axis. A first component is mounted at the distal end of the main shaft to provide for back and forth movement relative to the axis, in a first radial direction. After the first component has been so moved, it can then be held in a predetermined position. There is also a second component that is mounted more distally on the first component, for back and forth movement in a second radial direction. In this case, the second radial direction is substantially perpendicular to the first radial direction. Like the first component, after the second component has been moved, it can also then be held in a predetermined position. Along with this combination, the second end of the post is mounted on the second component for universal rotation thereon. Also, there is a clamping means on the articulating tool for holding the second end of the post on the second component in a fixed manner. With the coordinated operation and manipulation of the first component, the second component, and the clamp, the articulating tool is able to spatially orient the prosthetic tooth, as desired. Preferably, the first component is moved by the action of a lead screw, while the second component is moved by a rack and pinion. Alternatively, the second component can be moved by the action of a lead screw, while the first component is moved by a rack and pinion. In either case, it is desirable that both the first component and the second component of the articulating tool be accessible for manipulation from the same direction.

In the manufacture and operation of the device of the present invention, a plurality of articulating tools in combination with their respective elongated posts, are positioned in an impression of the patient's dental structure. The teeth casting is then made such that an end of each elongated post is embedded in an individual tooth of the teeth casting. Next, the gum casting is made and, finally, the support casting is made. As mentioned above, the articulating tool will be embedded within the gum casting. Importantly, for the purposes of manipulating the first and second components and for the purpose of clamping the post, each articulating tool should be accessible through the front of the gum casting.

In order to use the device described herein, in preparation for the teeth being straightened, an original dental structure is created to replicate the actual dental structure of a patient. Based on this original dental structure, a user can then orient individual teeth in the teeth casting, as desired, to create a new interim dental structure. An appliance is then made of this new interim dental structure. The device can then be reconfigured, as desired, to create a subsequently different interim dental structure. Again, an appliance is made. In practice, the most recent interim dental structure is used as a new interim dental structure, and the reconfiguration process is repeated as many times as necessary. Specifically, appliances can be made for each interim dental structure until an appliance for a final dental structure is formed. Together, the various appliances create a series of differential shapes for dental structures that can be sequentially used by the patient to realign and straighten his/her teeth.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of an articulating tool engaged with a prosthetic tooth in accordance with the present invention;

FIG. 2 is a side elevation view of the articulating tool;

FIG. 3 is a front view of the articulating tool with portions shown in cross-section as seen along the line 3-3 in FIG. 1;

DESCRIPTION OF THE PREFERRED EMBODIMENTS

Figure 4:
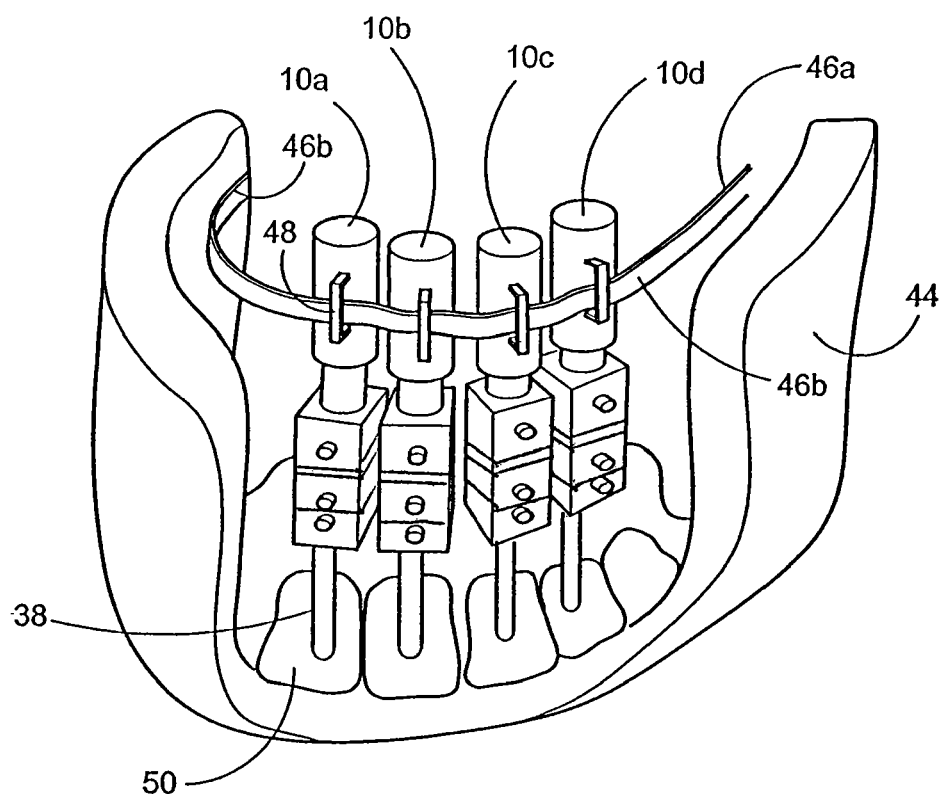
FIG. 4 is a perspective view of a dental impression tray with a plurality of articulating tools positioned therein, where portions of the tray have been removed for clarity.

Referring initially to FIG. 1, an articulating tool in accordance with the present invention is shown and designated 10. There it will be seen that the articulating tool 10 includes a main shaft 12 that defines an axis 14. Further, the tool 10 includes a component 16 that is mounted at the distal end of the shaft 12. For purposes of this disclosure, the proximal direction is taken to be in a positive z-direction (see FIG. 1), and the distal direction is therefore in the negative z-direction. As shown, the tool 10 also includes another component 18 that is mounted distally from the component 16. More specifically, a structural interconnect 20 is provided between the component 16 and the component 18. Additionally, the tool 10 includes a socket 22 that is integrally mounted distally on the component 18.

In FIG. 2, it can be clearly seen that the component 16 is associated with a lead screw 24 that is associated with the interconnect 20. With this connection, an appropriate rotation of the lead screw 24 will cause the component 16 to move back and forth in radial directions relative to the axis 14 (i.e. alternatively in the x-directions indicated by arrows 28 and 26). By cross-referencing FIG. 2 with FIG. 3, it will also be seen that the component 18 includes a pinion 30 that interacts with a saw-tooth rack 32 formed on the interconnect 20. With this connection, an appropriate rotation of the pinion 30 will cause the component 18 to move back and forth in radial directions relative to the axis 14 (i.e. alternatively in the y-directions indicated by arrows 34 and 36). Accordingly, movements of the component 16 will be perpendicular to the movements of the component 18.

As best appreciated by cross-referencing FIG. 1 with FIG. 3, the articulating tool 10 of the present invention is engageable with an elongated post 38 that is formed with a ball 40 at its proximal end. FIG. 3 shows that the ball 40 of the post 38 is positioned in the socket 22 of the articulating tool 10. Further, the tool 10 has a clamp screw 42 that can be rotated to tighten it against the ball 40. This then will hold the post 38 in a stationary orientation on the tool 10. Otherwise, as intended for the present invention, the ball 40 and socket 22 cooperate with each other to allow the post 38 to move in a universal rotation about a point at the center of the ball 40. As indicated, however, the clamp screw 42 can be manipulated to prevent such rotation.

At this point, it will be appreciated that the elongated post 38 can be selectively moved by the articulating tool 10 in several directions. In detail, translational movements of the post 38 can be made in radial directions, relative to the axis 14. And, rotational movement of the post 38 can be made relative to the center of ball 40. Specifically, a rotation of the lead screw 24 will move the interconnect 20, component 18 and socket 22 with post 38 in an x-direction, perpendicular to the axis 14. On the other hand, a rotation of the pinion 30 will move the component 18 and socket 22 with post 38 in a y-direction, also perpendicular to the axis 14. Finally, a rotation of the clamp screw 42 can be made to hold the post 38 stationary in the joint between the ball 40 of post 38 and the socket 22 of the tool 10.

Referring now to FIG. 4, it will be seen that the articulating tool 10 is to be used together with other such tools 10. The articulating tools 10a-d shown in FIG. 4, however, are only exemplary. In any event, as shown, it is envisioned that a plurality of tools 10 is properly positioned in a dental impression 44 that accurately replicates the dental structure of a patient (not shown) before corrective dental alignment procedures are taken. Specifically, the various tools 10 are held in the dental impression 44 by the holding wires 46a and 46b that interact with tie brackets 48 on the respective tools 10. As shown, a tie bracket 48 is formed on each of the respective articulating tools 10 for this purpose. Importantly, and using the articulating tool 10a as an example, the elongated posts 38 that are associated with respective articulating tools 10 are positioned in the dental impression 44 so that the extreme distal end of the post 38 is positioned in an individual tooth impression 50.

Figure 5:
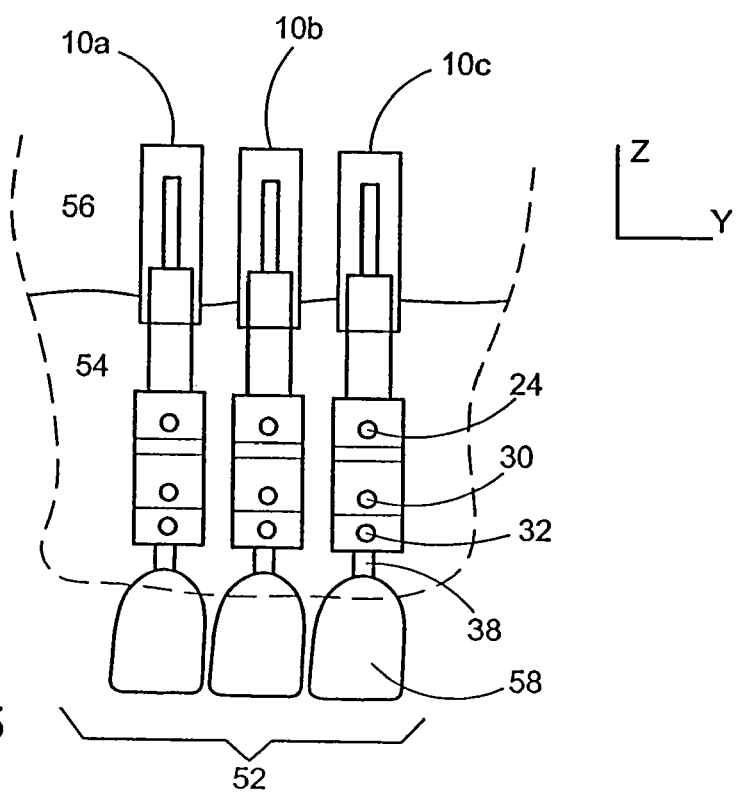
FIG. 5 is a front view showing a plurality of articulating tools in combination with a teeth casting, a gum casting and a support casting, in accordance with the present invention.

FIG. 5 shows the result that is obtained when the articulating tools 10 are embedded in the various castings of the device of the present invention. Specifically, FIG. 5 shows a teeth casting 52 that is made to replicate the individual teeth in the patient's dental structure. Preferably, the teeth casting 52 is made of a relatively rigid material, such as a hard durable urethane. As shown, the teeth casting 52 is made to cover and engage the distal end of the respective elongated posts 38. Next, a gum casting 54 is made. Unlike the teeth casting 52, the gum casting 54 is made of a relatively flexible material, such as a polyurethane elastomer. It needs to be noted here that most of the articulating tool 10 is actually embedded in the gum casting 54. Importantly, the gum casting 54 needs to extend over a portion of the elongated posts 38, and beyond the distal end of the articulating tool 10, so that the flexible material of the gum casting 54 can allow individual teeth in the teeth casting 52 to be moved relative to the articulating tool 10. Finally, there is a support casting 56. As envisioned for the present invention, the support casting 56 is made of the same rigid material that is used for the teeth casting 52. The import of the support casting 56 being to hold the various articulating tools 10 in a fixed relationship with each other.

Once the elongated posts 38 have been joined to the teeth casting 52, and the articulating tools 10 have been embedded in the gum casting 54 and are held by the support casting 56, individual teeth (e.g. prosthetic tooth 58) in the teeth casting 52 can be selectively manipulated. Specifically, with reference to FIG. 5, and as disclosed above with reference to FIGS. 1-3, a rotation of the lead screw 24 will move the prosthetic tooth 58 in or out of the plane of FIG. 5, in an x-direction. A rotation of the pinion 30 will move the prosthetic tooth 58 left or right in the plane of FIG. 5, in an y-direction. And a rotation of the clamp screw 42 will hold the prosthetic tooth 58 in whatever rotational orientation is selected for the elongated post 38. By selectively positioning each tooth in the teeth casting 52, a user is able to customize the reconfiguration of a dental structure. Further, a series of such reconfigured dental structures can be made, and used for the manufacture of appliances (not shown). The appliances can then be sequentially worn by a patient, in accordance with instructions from a dentist, for the purpose of straightening teeth in the patient's dental structure.

While the particular Method and Apparatus for Repositioning Teeth as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for reconfiguring a model dental structure which comprises:
    a casting of a plurality of teeth, wherein the teeth casting is made of a rigid material;
    a casting of a gum, wherein the gum casting is made of a flexible material and is positioned in contact with the teeth casting;
    a support casting made of the rigid material, wherein the support casting is positioned in contact with the gum casting, and wherein the gum casting is positioned between the teeth casting and the support casting;
    a plurality of elongated posts, with each post having a first end and a second end, wherein the first end of each post is embedded in a respective tooth of the teeth casting with the second end of the post extending therefrom and into the gum casting; and
    an articulating tool respectively engageable with the second end of each of the posts for selectively and independently orienting each post and the tooth therewith, to reconfigure the dental structure, and wherein the support casting contacts each articulating tool to stabilize the plurality of posts on the device.

2. A device as recited in claim 1 wherein the articulating tool comprises:
    a main shaft having a proximal end and a distal end, and defining an axis;
    a first component mounted on the distal end of the main shaft for back and forth movement in a first radial direction;
    a first means for selectively moving the first component to a predetermined position;
    a second component mounted distally on the first component for back and forth movement in a second radial direction, wherein the second radial direction is substantially perpendicular to the first radial direction, and wherein the second end of the post is mounted on the second component for universal rotation thereon;
    a second means for selectively moving the second component to a predetermined position; and
    a clamping means for fixedly holding the second end of the post on the second component to orient the prosthetic tooth.

3. A device as recited in claim 2 wherein the first moving means is a lead screw.

4. A device as recited in claim 2 wherein the second moving means is a rack and pinion.

5. A device as recited in claim 2 wherein said first moving means is the second moving means.

6. A device as recited in claim 1 wherein the rigid material is a hard durable urethane.

7. A device as recited in claim 1 wherein the flexible material is a polyurethane elastomer.

8. A method for manufacturing a system for orienting prosthetic teeth in a model dental structure which comprises the steps of:
    creating an impression of a plurality of teeth in a dental structure of a patient;
    positioning a plurality of articulating tools in the impression, wherein each tool includes a post and each post is positioned relative to a respective tooth defined in the impression;
    making a teeth casting of the plurality of teeth, wherein the teeth casting is made of a rigid material, and wherein each post is embedded in a respective tooth of the teeth casting;
    forming a gum casting, wherein the gum casting is made of a flexible material and is positioned in contact with the teeth casting to surround portions of each articulating tool; and
    establishing a support casting made of the rigid material, wherein the support casting is positioned in contact with the gum casting, and wherein the gum casting is positioned between the teeth casting and the support casting, and further wherein the support casting contacts each articulating tool to stabilize the plurality of posts on the device.

9. A method as recited in claim 8 wherein the rigid material is a hard durable urethane and the flexible material is a polyurethane elastomer.

10. A method as recited in claim 8 wherein an articulating tool comprises:
    a main shaft having a proximal end and a distal end, and defining an axis;
    a first component mounted on the distal end of the main shaft for back and forth movement in a first radial direction;
    a second component mounted distally on the first component for back and forth movement in a second radial direction, wherein the second radial direction is substantially perpendicular to the first radial direction;
    a post for holding the prosthetic tooth, the post having an end thereof swivel mounted on the second component for universal rotation about a point thereon; and
    a means for fixedly holding the post at the point on the second component to orient the prosthetic tooth.

11. A method as recited in claim 10 further comprising the steps of:
    selectively moving the first component to a predetermined position;
    selectively moving the second component to a predetermined position; and
    clamping the post holding means.

12. A method as recited in claim 10 wherein the first moving means is a lead screw.

13. A method as recited in claim 10 wherein the second moving means is a rack and pinion.

* * * * *